United States Patent [19]

Fleet

[11] Patent Number: 5,248,779
[45] Date of Patent: Sep. 28, 1993

[54] SYNTHESIS OF NOJIRIMYCIN DERIVATIVES

[75] Inventor: George W. J. Fleet, Oxford, United Kingdom

[73] Assignee: Monsanto Company, St. Louis, Mo.

[21] Appl. No.: 949,953

[22] Filed: Sep. 24, 1992

Related U.S. Application Data

[62] Division of Ser. No. 716,490, Jun. 17, 1991, Pat. No. 5,200,523.

[51] Int. Cl.$^5$ ............... C07D 211/36; C07D 211/40; C07D 211/54
[52] U.S. Cl. ................... 546/242; 546/243
[58] Field of Search ............... 546/220, 242, 243

[56] References Cited

U.S. PATENT DOCUMENTS 4,849,430 7/1989 Fleet et al. ............... 514/315
5,013,842 5/1991 Fleet et al. ............... 546/220

FOREIGN PATENT DOCUMENTS 276867 2/1988 Japan .
8703903 7/1987 PCT Int'l Appl. .

OTHER PUBLICATIONS

Broxterman et al., Recl. Trav. Chim., Pay-Bas 106, 571–576 (1987).
Bernotas & Ganem, Tetrahedron Lett. 26, 1123 (1985).
Saeki & Ohki et al., Chem. Pharm. Bull. 16, 2477 (1968).
Schmidt et al., Liebigs Ann. Chem. 1989, p. 423.
Inouye et al., Tetrahedron 24, 2125–2144 (1968).
Whistler & Gramera, J. Org. Chem. 29, 2609 (1964).
Nayak & Whistler, Ibid. 33, 3582 (1968).
Fleet & Smith, Tetrahedron 43, 971–978 979–990 (1987).
Fleet et al., Tetrahedron 45, 327 (1989).
McOmie, Protective Group in Org. Chem., Plenum Press, 1973, pp. 96, 98, 103.

Primary Examiner—C. Warren Ivy
Assistant Examiner—Raymond Covington
Attorney, Agent, or Firm—Scott J. Meyer

[57] ABSTRACT

Nojirimycin δ-lactam and deoxynojirimycin are each synthesized from 5,6-anhydro-3-O-benzyl-1,2-O-isopropylidene-L-idofuranose as a divergent intermediate by a method which comprises formation of the piperidine ring by connection of nitrogen between C-1 and C-5 with inversion of configuration at C-5 to form nojirimycin δ-lactam or between C-2 and C-6 with inversion of configuration at C-2.

3 Claims, No Drawings

SYNTHESIS OF NOJIRIMYCIN DERIVATIVES

This is a division of application Ser. No. 07/716,490, filed Jun. 17, 1991 now U.S. Pat. No. 5,200,523.

BACKGROUND OF THE INVENTION

This invention relates to a method for the synthesis of nojirimycin derivatives and, more particularly, to the synthesis of deoxynojirimycin and nojirimycin δ-lactam from an epoxide derivative of L-idofuranose.

Deoxynojirimycin is a well-known glucosidase inhibitor [Ishida et al., *J. Antibiot. Ser. A*20, 66 (1967)]. Recently, it has been suggested as having potential use for the treatment of acquired immune deficiency syndrome (AIDS). See, e.g., Sunkara et al., *Biochem. Biophys. Res. Commun.* 148(1), 206-210 (1987); Tyms et al., *Lancet*, Oct. 31, 1987, pp. 1025-1026; Walker et al., *Proc. Natl. Acad. Sci. USA* 84, 8120-8124 (1987); and Gruters et al., *Nature* 330, 74-77 (1987).

Derivatives of deoxynojirimycin also have been reported to have potential use as anti-AIDS drugs based on inhibitory activity against human immunodeficiency virus (HIV). See, e.g., the report of such use of the N-methyl derivative of deoxynojirimycin in PCT Inter. Appln. WO 87/03903, published Jul. 2, 1987, and the substantially more effective anti-HIV activity of the N-butyl derivative of deoxynojirimycin as disclosed in U.S. Pat. No. 4,849,430.

The properties of deoxynojirimycin as a glucosidase inhibitor and the recognition of the potential applications of such compounds have led to considerable studies on the synthesis of nojirimycin derivatives. See, e.g., Paulsen et al., *Chem. Ber.* 100, 802 (1967); Kinast and Schedel, *Angew. Chem. Int. Edit.* 20, 805 (1981); Vasella and Voeffray, *Helv. Chim. Acta* 65, 1134 (1982); Bernotas and Ganem, *Tetrahedron Lett.* 26, 1123 (1985). Although the most common strategy for the synthesis of nojirimycin derivatives has been by the introduction of nitrogen with retention of configuration at C-5 of glucose [Saeki and Ohki, *Chem. Pharm. Bull.* 16, 2477 (1968); Schmidt et al., *Liebigs Ann. Chem.* 1989, 423], the only reported stereospecific synthesis of nojirimycin δ-lactam was by hypoiodite oxidation of nojirimycin [Inouye et al., *Tetrahedron* 24, 2125 (1968)].

BRIEF DESCRIPTION OF THE INVENTION

In accordance with the present invention, nojirimycin δ-lactam (1) and deoxynojirimycin (3) are each synthesized from an epoxide derivative of L-idofuranose (2), namely 5,6-anhydro-3-O-benzyl-1,2-O-isopropylidene-L-idofuranose (4). By this synthesis, the epoxide (4) is used as a divergent intermediate as follows:

A. to produce nojirimycin δ-lactam (1) by a synthesis method which comprises formation of the piperidine ring by connection of nitrogen between C-1 and C-5 with inversion of configuration at C-5, which is the equivalent of double inversion at C-5 of glucose, or B. to produce deoxynojirimycin (3) by a synthetic method which comprises formation of the piperidine ring by connection of nitrogen between C-2 and C-6 with inversion of configuration at C-2.

The epoxide (4) starting material is a known compound which can be prepared essentially by the well-known published method described by Whistler and Gramera, *J. Org. Chem.* 29, 2609 (1964).

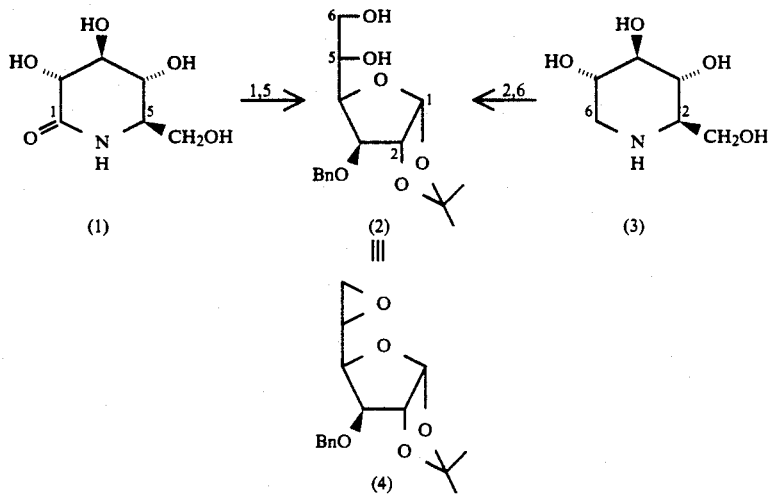

Bn = CH₂Ph

In a preferred embodiment of the synthesis of nojirimycin δ-lactam (1), the following reaction steps are carried out:

a) Reacting epoxide (4) with sodium hydride and benzyl alcohol to give the dibenzyl idofuranose (5), b) Esterifying the free hydroxyl of the dibenzyl idofuranose (5) with trifluoromethane sulfonic anhydride to provide triflate (6), c) Reacting triflate (6) with azide ion, e.g. sodium azide, to afford the gluco-azide (7), d) Removing the isopropylidene protecting group from the gluco-azide (7) by acid hydrolysis, e.g. aqueous trifluoroacetic acid, to give the is corresponding lactol, e) Oxidizing the resulting lactol with bromine to give the azidolactone (8), f) Reducing the azidolactone (8) by tin (II) chloride followed by treatment with potassium carbonate to provide the dibenzyl lactam (9), and g) Removing the benzyl groups by palladium catalyzed hydrogenation to give the desired nojirimycin δ-lactam (1).

In a preferred emobdiment of the synthesis of deoxynojirimycin (3), the following reaction steps are carried out:

a) Reacting epoxide (4) with azide ion, e.g. sodium azide, to give the ido-azide (10), b) Reacting the ido-azide (10) with sodium hydride, benzyl bromide and tetrabutylammonium iodide to afford the dibenzyl ether (11), c) Treating the dibenzyl ether (11) with methanolic hydrogen chloride to give methyl furanoside (12), d) Esterifying methyl furanoside (12) with trifluoromethane sulfonic anhydride to give triflate (13), e) Reducing triflate (13) with tin (II) chloride to give aminotriflate (14), f) Reacting aminotriflate (14) with sodium acetate to give bicyclic amine (15), g) Reacting bicyclic amine (15) with benzyl chloroformate to give protected carbamate (16), h) Subjecting protected carbamate (16) to acid hydrolysis, e.g. with trifluoroacetic acid, followed by reduction with sodium borohydride to give the protected deoxynojirimycin (17), and i) subjecting the protected deoxynojirimycin (17) to palladium catalyzed hydrogenation to provide the desired deoxynojirimycin (3).

Other such suitable reactants for use in the foregoing syntheses of nojirimycin δ-lactam and deoxynojirimycin will be apparent to the person skilled in the art after reading the present disclosure. These reactants are generally used in proportions such as to satisfy the stoichiometry of the above reaction steps. Thus, other suitable azide cations for use in these reactions are potassium, tetra-butylammonium, lithium and the like. Other suitable organic solvents for use in the synthesis are N-methylpyrrolidine, acetone, acetonitrile, dimethylsulfoxide and the like. Other suitable protecting groups can be introduced by reaction with ketones and dialkylketones such as for example, acetone, 3-pentanone, dihexylketone, cyclohexanone and the like.

DETAILED DESCRIPTION OF THE INVENTION

The invention is conveniently illustrated by the following description of preferred embodiments in which the 5,6-anhydro-3-O-benzyl-1,2-O-isopropylidene-β-L-idofuranose or its immediate precursor, 6-O-benzyl-3-O-5-O-methanesulfonyl-1, 2-O-isopropyl-idene-α-D-glucofuranose, are used to prepare nojirimycin δ-lactam (1) and deoxynojirimycin (3).

These illustrative embodiments of the invention were carried out by reactions, as follows, in which compound numbers in parenthesis correspond to the compounds shown by structure herein.

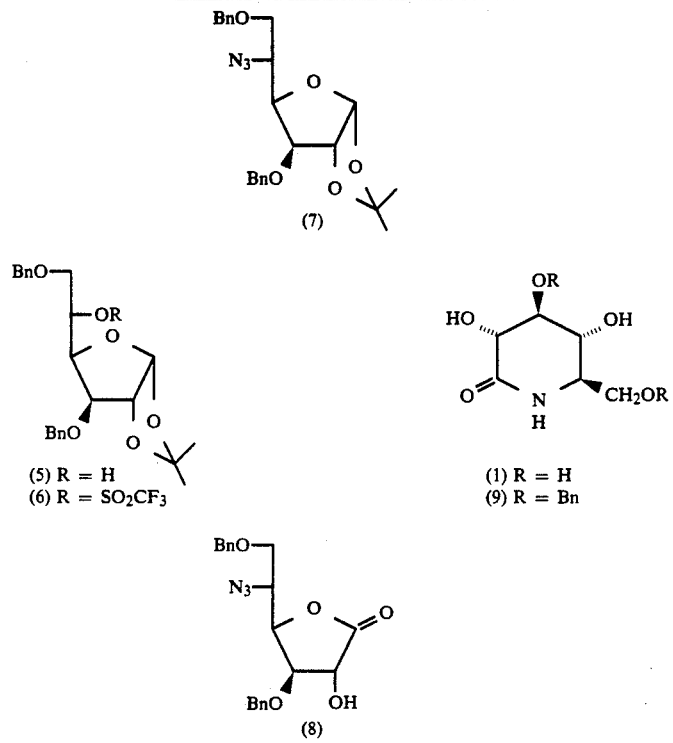

A. Synthesis of nojirimycin δ-lactam (1).

Treatment of epoxide (4) with sodium hydride and benzyl alcohol in dimethylformamide gave the dibenzyl ido-furanose (5) m.p. 70°–71° C. (lit.* 74° C.) in an overall yield of 49% from diacetone glucose. [*Saeki and Ohki, Chem. Pharm. Bull. 16, 2477 (1968).] Esterification of the free hydroxyl group in (5) with trifluoromethane sulphonic anhydride in dichloromethane in the presence of pyridine, followed by treatment of the resulting triflate (6) with sodium azide in dimethylformamide afforded the gluco-azide (7), m.p. 66°–67° C. (lit.* 74° C.) in 75% yield. [*Naryah and Whistler, J. Org. Chem. 33 3582 (1968).] The isopropylidene protecting group was removed from (7) by hydrolysis with aqueous trifluoroacetic acid and the resulting lactol was oxidized by bromine in aqueous dioxane in the presence of barium hydroxide to give the azidolactone (8), $v_{max}$ 2100 (N₃), 1790 (C=O) cm⁻¹, in 74% yield.

$^{13}$C NMR of (8) (CDCl₃), non-aromatic carbons: δ 175.07 (s, C=O), 79.47 (d), 78.38 (d), 71.62 (d), 59.79 (d), 73.58 (t), 72.59 (t), 69.73 (t).

Reduction of the azidolactone (8) by tin (II) chloride in methanol [Maiti et al., *Tetrahedron Lett.* 27, 1423 (1986)], followed by treatment with potassium carbonate, gave the dibenzyl lactam (9), m.p. 110°–112° C., $[\alpha]_D^{20}$ +10.8° (c, 0.83 in CHCl$_3$), in 56% yield. $^{13}$C NMR of (9) (CDCl$_3$), non-aromatic carbons: δ 172.15 (s, C=O), 81.15 (d), 72.13(d), 68.15 (d), 55.00 (d), 74.22 (t), 73.46 (t), 70.95 (t). The benzyl groups were removed from (9) by hydrogenation in ethanol in the presence of palladium black to give nojirimycin δ-lactam (1), m.p. 204°–205° C., $[\alpha]_D^{20}$ +57° (c, 0.63 in H$_2$O) [lit* m.p. 202°–204° C., $[\alpha]_D^{25}$ +60° (H$_2$O)]. [*Inouye et al., *Tetrahedron* 24, 2125–2144 (1968)]. $^{13}$C NMR of (1) (D$_2$O),: δ 174.38 (s, C=O), 74.06 (d), 71.39 (d), 68.25 (d), 57.66 (d), 61.04 (t).

B. Synthesis of deoxynojirimycin (3).

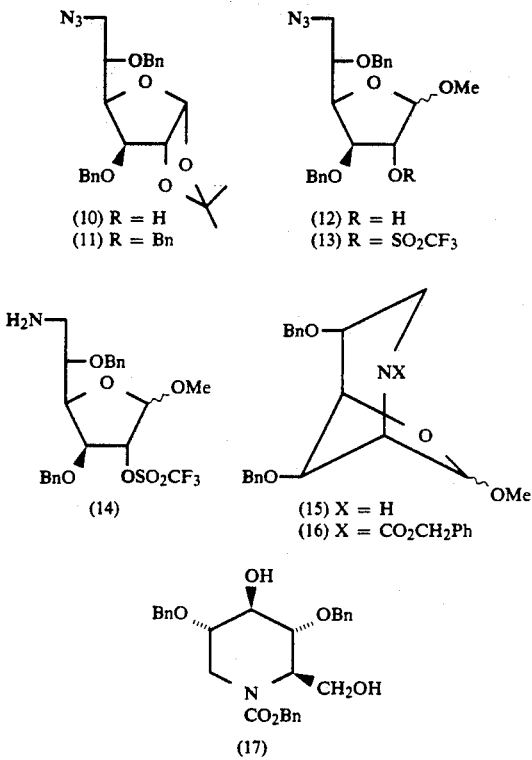

The formation of a piperidine ring between C-2 and C-6 of sugar involves nucleophilic substitution by nitrogen at C-2. Although intermolecular displacement of triflate at C-2 of a furanose by azide occurs smoothly if the anomeric substituent is cis- to the leaving group, the displacement if the leaving group is trans- to the anomeric substituent is very much less efficient. See Fleet and Smith, *Tetrahedron* 43, 971 (1987); Fleet et al., *Tetrahedron* 43, 979 (1987). In contrast, intramolecular substitution of a triflate at C-2 by an amino function at C-6 occurs readily with both furanose anomers. Thus, introduction of nitrogen at C-6 initially, rather than at C-2, is the preferred method. See Fleet et al., *Tetrahedron* 45, 327 (1989).

Reaction of the epoxide (4) with sodium azide in dimethylformamide gave the ido-azide (10) (87% yield) which with sodium hydride, benzyl bromide and tetrabutylammonium iodide in tetrahydrofuran afforded the dibenzyl ether (11), m.p. 40°–41° C., in 91% yield. Treatment of (11) with methanolic hydrogen chloride gave the methyl furanosides (12) (67% yield) which is were esterified with trifluoromethane sulphonic anhydride to give the corresponding triflates (13) (88% yield for α anomer; 54% yield for β anomer).

The anomer ratio of (12) was α:β 2:1. The subsequent reactions were carried out on both anomers separately and on the mixture; there is no advantage in separating the anomers.

Reduction of a mixture of the azidotriflates (13) with tin (II) chloride in methanol gave the aminotriflates (14) which on stirring with sodium acetate in ethanol gave the bicyclic amine (15); reaction with benzyl chloroformate gave the protected carbamates (16) [67% overall yield from (13)]. Thus, the intramolecular cyclization of both anomers occurs smoothly, even though the two O-benzyl substituents would be in 1,3-diaxial relationship in the bicyclic amine. Subsequent hydrolysis of the furanosides (16) by trifluoroacetic acid in aqueous dioxane in the lactol, followed by reduction by sodium borohydride in ethanol afforded the protected deoxynojirimycin (17), m.p. 85°–87° C. $[\alpha]_D^{20}$ 0.0° (c 0.29 in MeOH) in 49% yield. Subsequent hydrogenation of (17) in acetic acid in the presence of palladium black gave, after purification by ion exchange chromatography, deoxynojirimycin (3), identical with authentic material and readily crystallized as the hydrochloride, m.p. 204°–205° C. (lit.* 203°–206° C.). [*Fleet et al., *Tetrahedron* 43, 971 (1987); Ibid. 43, 979 (1987)]. $^{13}$C NMR of (3) as free base (D$_2$O),: δ 79.0 (d), 72.1 (d), 71.1 (d), 61.9 (t), 61.0 (d), 49.2 (t, C-1). $^{13}$C NMR of (3) as hydrochloride (D$_2$O),: δ 77.1 (d), 68.6 (d), 67.8 (d), 60.8 (d), 58.5 (d), 46.7 (t, C-1).

The following examples will further illustrate the invention in greater detail although it will be appreciated that the invention is not limited to these specific examples. Examples 1–4 illustrate the preparation of the divergent intermediate epoxide (4). Examples 5–14 illustrate the preparation of deoxynojirimycin (3), whereas Examples 15–19 illustrate the preparation of nojirimycin δ-lactam (1).

EXAMPLE 1

3-O-Benzyl-1,2:5,6-di-O-isopropylidene-α-D-glucofuranose

Sodium hydride (60% suspension in oil, 10.8 g, 0.23 mol) was washed with hexane (3×20 ml) under nitrogen before being suspended in dry, freshly distilled, tetrahydrofuran (60 ml). Diacetone glucose (50 g, 0.19 mol) dissolved in tetrahydrofuran (300 ml) was then added over 1 hour with cooling. Benzyl bromide (25 ml, 0.21 mmol) and tetrabutylammonium iodide (0.3 g) were then added and the reaction stirred under reflux for 2 hours. T.l.c. (50%, ethyl acetate/hexane) then showed no starting material ($R_f$ 0.1) and one product ($R_f$ 0.9). Methanol was added and the reaction stirred for 5 minutes at room temperature. Dilution with diethyl ether (200 ml) and filtration though celite followed by removal of the solvent in vacuo gave the crude diacetonide, 3-O-benzyl-1,2:5,6diOisopropylidene-α-D-glucofuranose, which was used without further purification.

EXAMPLE 2

3-O-Benzyl-1,2-O-isopropylidene-α-D-glucofuranose

The crude diacetonide product of Example 1 was dissolved in a solution of concentrated hydrochloric acid (10 ml), water (100 ml) and methanol (400 ml) and stirred for 16 hours at room temperature. T.l.c. (50%, ethyl acetate/hexane) then showed no starting material (R$_f$ 0.9) and one major product R$_f$ 0.2). The solution was then neutralized with ammonia solution (SG 0.88) before the solvent was removed in vacuo. The resultant oil was taken up in ethyl acetate (500 ml) and washed with water (200 ml) and brine (400 ml), before being dried (sodium sulphate). Removal of the solvent in vacuo gave the crude diol, 3-O-benzyl-1,2-O-isopropylidene-α-D-glucofuranose, (62 g) as a syrup which was used without further purification. [α]$_D^{20}$ −50.8° (c, 1.24 in CHCl$_3$), $\nu_{max}$: 3500, 1075, 1020 cm$^{-1}$.

EXAMPLE 3

6-O-Benzoyl-3-O-benzyl-5-O-methanesulphonyl-1,2-O-isopropylidene-α-D-glucofuranose To the diol product of Example 2 (62 g, 0.2 mmol) in dry pyridine (500 ml) at 0° C. was added, dropwise and with stirring, benzoyl chloride (19.6 ml, 0.2 mmol). After 6 hours no diol (R$_f$ 0.1) remained by t.l.c. (diethyl ether/hexane, 50%). Methanesulphonyl chloride (18.7 ml, 0.3 mmol) was added dropwise and the reaction stirred for a further 12 hours at room temperature. The pyridine was then removed in vacuo, the resultant oil being taken up in ethyl acetate (400 ml) and washed with dilute aqueous hydrochloric acid (150 ml), water (150 ml), and brine (250 ml). The solution was then dried (sodium sulphate), filtered and the solvent removed in vacuo to give an amber oil which was crystallized to give the methylbenzoate, 6-O-benzoyl-3-O-benzyl-5-O-methanesulphonyl-1,2-O-isopropylidene-α-D-glucofuranose as a white crystalline solid (81 g, 90%), m.p. 89°-90° C. [α]$_D^{20}$ −10.70° (c, 3.3 in CHCl$_3$). $\nu_{max}$: 1725, 1360, 1270, 1180, 1115, 1075, 1025, 910 cm$^{-1}$. (Found: C, 58.24; H, 5.78%. C$_{24}$H$_{28}$O$_9$S requires C, 58.52; H, 5.73%).

EXAMPLE 4

5,6-Anhydro-3-O-benzyl-1,2-O-isopropylidene-β-L-idofuranose (4)

To a solution of the mesylbenzoate product of Example 3 (17.0 g, 34.5 mmol) in freshly distilled, dry, dimethylformamide (150 ml) was added sodium methoxide (3.6 g, 62.2 mmol). The reaction was then stirred at room temperature, under nitrogen, for 1 hour. The solvent was then removed in vacuo and the resultant oil taken up in diethyl ether (150 ml). The solution was then wased with water (50 ml) which was back extracted with diethyl ether (30 ml). The combined ethereal extracts were then washed with brine (5×60 ml), dried (sodium sulphate) and the solvent removed in vacuo to give the crude epoxide. Purification by flash chromatography (0–30%, diethyl ether/hexane) then gave the epoxide, 5,6-anhydro-3-O-benzyl-1,2-O-isopropylidene-β-L-idofuranose (4), as a colorless oil (10 g, 99%). [α]$_D^{20}$ −71.7° (c, 0.26 in CHCl$_3$) [lit.* [α]$_D^{20}$ 70.5° (c, 2.6 in CHCl$_3$)], $\nu_{max}$: 1386, 1376, 1250, 858, 735 cm$^{-1}$. (Found: C, 65.70; H, 6.82%. C$_{16}$H$_{20}$O$_5$ requires C, 65.75; H, 6.84%). [*Whistler and Gramera, *J. Org. Chem.* 29, 2609 (1964).

EXAMPLE 5

6-Azido-3-O-benzyl-6-deoxy-1,2-O-isonropylidene-β-L-idofuranose (10)

To a solution of the epoxide (4), (12.6 g, 43 mmol) in freshly distilled, dry, dimethylformamide (190 ml) was added sodium azide (5.6 g, 86 mmol). The reaction was then stirred for 48 hours, under nitrogen, at 85° C. T.l.c. (50%, diethyl ether/hexane) then showed no starting almterial (R$_f$ 0.30) and one product (R$_f$ 0.25). The solvent was then removed in vacuo, the resultant oil being taken up in diethyl ether. The ethereal solution was then washed with water (60 ml) which was back extracted with diethyl ether (50 ml). The combined ethereal extracts were then washed with brine (5×100 ml), dried (sodium sulphate) and the solvent removed in vacuo. Purification by flash chromatography then gave 6-azido-3-O-benzyl-6-deoxy-1,2-O-isopropylidene-β-L-iodofuranose (10), as a colorless oil (12.5 g, 87%). [α]$_D^{20}$ −69.0° (c, 0.65 in CHCl$_3$) (lit.* [α]$_D^{25}$ 68.8° (c, 4.3 in CHCl$_3$)). $\nu_{max}$: 3500, 2100, 1376, 1353, 741 cm$^{-1}$. (Found C, 57.36; H, 6.51; N, 12.84%. C$_{16}$H$_{21}$N$_3$O$_5$ requires C, 57.30; H, 6.27; N, 12.50%). [*Saeki and Ohki, *Chem. Pharm. Bull.* 16, 2477 (1968)].

EXAMPLE 6

6-Azido-6-deoxy-3,5-di-O-benzyl-1,2-O-isopropylidene-β-L-idofuranose (11)

To a suspension of sodium hydride (60% in oil, 1.9 g, 39.8 mmol) in tetrahydrofuran (30 ml) was added, dropwise and with cooling, a solution of the azide (10) (12.5 g, 36.2 mmol) in tetrahydrofuran (170 ml). Tetrabutylammonium iodide (20 mg) was then added followed by benzyl bromide (4.7 ml, 39.8 mmol). The turbid solution was refluxed gently for 2 hours by which time t.l.c (50%, diethyl ether/hexane) showed no starting material (R$_f$ 0.25) and one product (R$_f$ 0.5). After cooling, methanol (5 ml) was added carefully and the reaction stirred for a further 5 minutes. Diethyl ether (200 ml) was then added and the reaction filtered through silica topped with celite. The silica was then washed repeatedly with diethyl ether until no product remained. The solvent was then removed in vacuo to give a yellow oil which was purified by flash chromatography (0–30%, diethyl ether/hexane) followed by recrystallization to give 6-azido-6-deoxy-3,5-di-O-benzyl-1,2-O-isopropylidene-β-L-idofuranose (11), as a white crystalline solid (12 g, 91%), m.p. 40°–41° C. (30/40 petrol, trace of diethyl ether). [α]$_D^{20}$ −45° (c, 0.53 in CHCl$_3$). $\nu_{max}$ (CHCl$_3$): 2100, 1370, 1350, 738 cm$^{-1}$. (Found C, 65.07; H, 6.46; N, 11.5%. C$_{23}$H$_{27}$N$_3$O$_5$ requires C, 64.94; H, 6.35; N, 9.88%).

EXAMPLE 7

Methyl 6-azido-6-deoxy-3,5-di-O-benzyl-α- and β-L-idofuranoside (12)

The azide (11) (0.6 g, 1.4 mmol) was stirred in a solution of freshly prepared methanolic HCl (1M, 30 ml) for 2 hours at room temperature. T.l.c. (50%, diethyl ether/hexane) then showed no starting material (R$_f$ 0.5) and 2 products (R$_f$ 0.35, 0.25). The solvent was then removed in vacuo and the crude products purified by flash chromatography (0–70%, diethyl ether/hexane) to give methyl-6-azido-6-deoxy-3,5-di-O-benzyl-α-L-idofuranoside (12α), and methyl 6-azido-6-deoxy-3,5-di-O-benzyl-β-L furanoside (12β), as colorless oils (260 mg, 46%, less polar, α) (120 mg, 21%, more polar, β). Less polar anomer. [α]$_D^{20}$ +140° (c, 0.48 in CHCl$_3$). $\nu_{max}$: 3450, 2100, 735, 690 cm$^{-1}$. (Found C, 63.07; E, 6.25; N, 10.30%. C$_{21}$H$_{25}$N$_3$O$_5$ requires C, 63.15; H, 6.26; N, 10.52%).

EXAMPLE 8

Methyl 6-azido-6-deoxy-3,5-di-O-benzyl-2-O-trifluormethanesulphonyl-α and β-L-idofuranoside (13α and β).

To a solution of the azidoalcohol (12) (0.78 g, 1.9 mmol) in freshly distilled, dry, dichloromethane (30 ml) was added dry pyridine (0.3 ml, 3.8 mmol). The solution was then cooled to −30° C. under nitrogen and trifluoromethanesulphonic anhydride (0.5 ml, 2.9 mmol) added slowly. After 1 hour at this temperature, t.l.c (50%, diethyl ether/hexane) showed no starting material ($R_f$ 0.2) and one product ($R_f$ 0.65). The solution was then washed successively with dilute aqueous hydrochloric acid (10 ml), water (10 ml) and brine (20 ml). Drying (sodium sulphate) followed by removal of the solvent in vacuo yielded the crude triflate as a yellow oil. Purification by flash chromatography (0–40%, diethyl ether/hexane) yielded methyl-6-azido-3,5-di-O-benzyl-6-deoxy-2-O-trifluoromethanesulphonyl-α and β-L-idofuranoside (13α and β), as a colorless oil (875 mg, 88%). The more polar alcohol was triflated, using an identical procedure, in a yield of 54%. Less polar β-anomer $[α]_D^{20}$ +108° (c, 0.42 in CHCl$_3$). $ν_{max}$: 2115, 1420, 740 cm$^{-1}$. More polar α-anomer $[α]_D^{20}$ −39° (c, 0.27 in CHCl$_3$). $ν_{max}$: 2105, 1420, 742, 703 cm$^{-1}$.

EXAMPLE 9

Methyl 6-amino-3,5-di-benzyl-6-deoxy-2-O-trifluoromethanesulphonyl-L-idofuranoside (14)

To a solution of the azidotriflate (13) (320 mg, 0.6 mmol) in dry methanol (3 ml) was added anhydrous stannous chloride (170 mg, 0.9 mmol). The reaction was then stirred for 12 hours at room temperature. The solvent was then removed in vacuo and the amine taken up in diethyl ether (20 ml). The solid tin residues were then removed by centrifuging. Removal of the solvent and purification by flash chromatography (0–30%, methanol/chloroform) then gave methyl 6-amino-6-deoxy-3,5-di-O-benzyl-2-O-trifluoromethanesulphonyl-L-idofuranoside (14) as a foam. $ν_{max}$: 1420, 750, 700 cm$^{-1}$.

EXAMPLE 10

Methyl 3,5-di-O-benzyl-2,6-dideoxy-2,6-imino-1-gulofuranoside (15)

To a solution of the aminotriflate (14) in ethanol (10 ml) was added sodium acetate (148 mg, 1.8 mmol). The solution was then stirred for 12 hours at 50° C. The solvent was then removed in vacuo to give Methyl 3,5-di-O-benzyl-2,6-dideoxy-2,6-imino-L-gulofuranoside (15), which was used without purification in the next example, below.

EXAMPLE 11

Methyl N-benzyloxycarbonyl-3,5-di-O-benzyl-2,6-dideoxy-2,6-imino-L-gulofuranoside (16)

To the crude amine (15), in a solution of diethyl ether:saturated sodium bicarbonate (3:2, 20 ml), was added benzylchloroformate (0.2 ml, 1.2 mmol). The reaction was then stirred, at such a rate as to make it one phase, for 2 hours. The aqueous phase was then separated and washed with diethyl ether (3×10 ml). The combined ethereal layers were then dried (sodium sulphate) and the solvent removed in vacuo. Purification by flash chromatography (0–50%, diethyl ether/hexane) then yielded methyl N-benzyloxycarbonyl-3,5-di-O-benzyl-2,6-deoxy-2,6-imino-L-gulofuranoside (16), as a colorless oil (200 mg, 67% from azidotriflate). $ν_{max}$ (CHCl$_3$): 1685, 750, 700 cm$^{-1}$.

EXAMPLE 12

N-Benzyloxycarbonyl-3,5-di--O-benzyl-2,6-dideoxy-2,6-imino-L-gulofuranoside

The methyl derivative (16) (400 mg, 0.82 mmol) was stirred in water:1,4-dioxane:trifluoroacetic acid (1:1:1, 6 ml) for 2 hours at room temperature. T.l.c. (60%, diethyl ether/hexane) then showed no starting material ($R_f$ 0.4) and several products ($R_f$ 0.3). Water (15 ml), dichloromethane (30 ml) and sodium acetate (1.2 g, 15.0 mmol) were then added and the reaction stirred for a further 10 minutes. The aqueous layer was then removed and washed with dichloromethane (3×15 ml). The combined organic extracts were then dried (sodium sulphate) before the solvent was removed in vacuo. Purification by flash chromatography (0–80%, diethyl ether/hexane) then gave the lactol, N-Benzyloxycarbonyl-3,5-di-O-benzyl-2,6-dideoxy-2,6-imino-L-gulofuranoside, as an oil (238 mg, 61%).

EXAMPLE 13

N-Benzyloxycarbonyl-2,4-di-O-benzyl-1,5-dideoxy-1,5-imino-D-glucitol (17)

The lactol product of Example 12 (238 mg, 0.5 mmol) was stirred in ethanol (8 ml) with sodium borohydride (19 mg, 0.5 mmol) for 15 minutes. T.l.c. (diethyl ether) then showed no starting material ($R_f$ 0.5) and one product ($R_f$ 0.2). Ammonium chloride was then added and the reaction stirred for a further 15 minutes. The solvent was then removed in vacuo and the resultant gum azeotroped with carbon tetrachloride (3×5 ml). The gum was then taken up in ethyl acetate and filtered through celite. Flash chromatography (0–90%, ethyl acetate/hexane) then gave N-benzyloxycarbonyl-2,4-di-O-benzyl-1,5-dideoxy-1,5-imino-D-glucitol (17), as a colorless oil which crystallized on standing (200 g, 82%). m.p. 85°–87° C. $[α]_D^{20}$ 0.0° (c, 0.29 in MEOH). $ν_{max}$ (KBr): 3300, 1680, 750, 700 cm$^{-1}$. (Found: c, 70.36; H, 6.80; N, 2.77%. C$_{28}$H$_{31}$NO$_6$, requires C, 70.44; H, 6.50; N, 2.94%).

EXAMPLE 14

1,5-Dideoxy-1,5-imino-D-glucitol (3)

The diol (17) (580 mg, 1.2 mmol) was stirred in glacial acetic acid (30 ml) in the presence of palladium black (100 mg) under hydrogen for 3 days, by which time no starting material ($R_f$ 0.2) remained by t.l.c. (diethyl ether). Filtration and removal of the solvent then gave a gum which was purified by ion exchange chromatography with Dowex 50(H+) followed by Amberlite CC-400(Cl−) resins to give 1,5-dideoxy-1,5-imino-D-glucitol (3) (188 mg, 95%), which was crystallized as its hydrochloride salt. m.p. 204°–205° C. (lit.* 203°–206° C.). All spectroscopic data were identical to that of authentic material. $^{13}$C NMR (D$_2$O) free base δ: 79.0, 72.1, 71.1 (3d, C-2, C-3, C-4), 61.9 (t, C-6), 61.0 (d, C-5), 49.2 (t, C-1). Hydrogen chloride salt δ: 77.1, 68.6, 67.8 (3d, C-2, C-3, C-4), 60.8 (d, C-5), 58.5 (t, C-6), 46.7 (t, C-1). [*Fleet et al., *Tetrahedron* 43, 979 (1987)].

EXAMPLE 15

3,6-Di-O-benzyl-1,2-O-isopropylidene-β-L-idofuranose (5)

A 60% oil dispersion of sodium hydride (10 g, 0.22 mole) was placed in a round bottom (RB) flask and washed three times with petroleum (60/80). Freshly distilled DMF (250 ml) was added and the mixture stirred magnetically while cooling on a dry ice/isopropanol bath. Benzyl alcohol (2.3 ml, 0.22 mole) was added portionwise while flushing the system with dry nitrogen. The mixture was stirred on the cooling bath for 10–20 min while the $H_2$ evolution slowed down. The bath was then removed and the mixture stirred for about 1 h before adding solid 6-O-benzoyl-3-O-benzyl-1,2-isopropylidene-5-O-methanesulphonyl-α-D-glucofuranose (see Example 3, above) (49.2 g, 0.10 mole). After about 1½ h at RT the starting material had gone completely to the 5,6-epoxide (4), but there was only a trace of the 6-O-benzyl-5-ol product. The mixture was heated at 80° C. for 2 h when t.l.c. showed a complete reaction. The reaction was partitioned between ice water (700 ml) and ether (700 ml) and the layers left to separate overnight. The organic layer was washed with brine (700 ml) and anhydrous $MgSO_4$ and charcoal were added. The mixture was filtered through celite and evaporated to dryness. The title product (5) was crystallized from ether (75 ml) and redistilled petroleum ether (60/80) (150 ml). Yield (1st crop) 25 g, (2nd crop) 5 g, 75%; m.p. 70°–71° C. $[\alpha]_D^{20}$ −4.0° (c, 3.0, $CHCl_3$).

EXAMPLE 16

5-Azido-3,6-di-O-benzyl-5-deoxy-1,2-O-isopropylidene-α-D-glucofuranose (7)

3,6-Di-O-benzyl-1,2-O-isopropylidene-β-L-idofuranose (5) (54.8 g, 0.14 mole) was dissolved in dry dichloromethane (400 ml). Dry pyridine (23 ml, 0.29 mole) was added and the mixture cooled on an ice/salt bath under dry nitrogen. Trifluoromethane sulphonic anhydride (27 ml, 0.16 mole) was added and the reaction left to reach 0° C. for approximately 2 h. Methanol (10 ml) was added and the reaction allowed to stand for ½ h. The reaction mixture was washed with ice water (2×500 ml), dried ($MgSO_4$) and evaporated to dryness. Azide displacement: The crude 5-O-triflate (6) was dissolved in freshly distilled DMF (250 ml). The solution was stirred and cooled on ice. Sodium azide (18 g, 0.28 mole) was added and the mixture left stirring to reach RT overnight. The DMF was evaporated off under high vacuum and the residue partitioned between ethyl acetate (1 liter) and water (1 liter). The layers were separated and the organic layer washed once with brine (500 ml), dried ($MgSO_4$) and evaporated. Towards the end of the evaporation charcoal was added. The residue was dissolved in ether and filtered through a 1 inch bed of silica 60 H topped with celite. The product was washed through with ether (4×200 ml). The ether was evaporated and the residue poured into a beaker and washed in with ether (100 ml), whereupon crystallization took place. Hot petroleum ether 60/80 (200 ml) was added and the solid dissolved, but on standing at RT and then upon refrigeration, recrystallization took place. The white crystals of the title compound (7) were isolated by filtration and washed with cold petroleum ether (60/80)/ether 2:1. Yield of first crop 40.1 g, 67%) 2nd crop 5.0 g, 8%; m.p. 66°–67° C. $[\alpha]_D^{20}$ −37° (c 1.0, $CHCl_3$); $\nu_{max}$ 2150, 2100, $N_3$. Found: C, 65.07; H, 6.77; N, 9.99%; calculated for $C_{23}H_{27}N_3O_5$: C, 64.92; H, 6.40; N, 9.88%.

EXAMPLE 17

5-Azido-3,6-di-O-benzyl-5-deoxy-D-glucono-γ-lactone (8)

Hydrolysis: 5-Azido-3,6-di-O-benzyl-5-deoxy-1,2-O-isopropylidene-α-D-glucofuranose (7) (2.13 g, 5.00 mmol) was placed in 100 ml RB flask. Trifluoroacetic acid (50%, 40 ml) was added and the mixture stirred at RT for 2 h. The flask was warmed gently until solution was clear. After ¼ h t.l.c. (pet/EToAC 1:1) showed complete reaction and the formation of one product, $R_f$ 0.4. Water (200 ml) was added and the mixture stirred while sodium bicarbonate (16.8 g, 0.2 mole) and sodium benzoate (14.4 g, 0.1 mole) were added slowly. The product was extracted into dichloromethalne (100 ml+2×50 ml) and evaporated.

Oxidation: The residue was redissolved in dioxane (40 ml) and water (20 ml). Two equivalents of barium hydroxide octahydrate (3.15 g, 10 mmol) was added and the flask wrapped in foil to exclude light and cooled on ice. Bromine (0.765 ml, 15 mmol) was added and the reaction left to reach RT over 4 h when t.l.c. (pet/EToAC 1:1) showed a complete reaction of the starting material, Rf 0.4 and one product, Rf 0.6. The excess bromine was destroyed with 1M sodium thiosulphate, the mixture centrifuged and the supernatant partitioned between ethyl acetate (100 ml) and water (100 ml). The organic phase was washed with brine (100 ml), dried ($MgSO_4$) and evaporated. The product was purified on a flash column eluting with pet/EtoAC 4:1 followed by 3:1. Yield of syrupy product (8) 1.42 g, 74%. $[\alpha]_D^{20}$ +14.5° (c, 1.5, $CHCl_3$). $\nu_{max}$ 3400, broad, OH; 2100, $N_3$; 1790, C—O.

EXAMPLE 18

5-Amino-5-deoxy-3,6-di-O-benzyl-D-glucono-δ-lactam (9)

5-Azido-5-deoxy-3,6-di-O-benzyl-D-glucono-γ-lactone (8) (383 mg, 1.00 mmol) was added to a suspension of tin (II) chloride in dry freshly distilled methanol (2 ml). The reaction was stirred overnight at room temperature when t.l.c. (pet/EtOAc 1:1) showed complete reaction of starting material, Rf 0.67, and two products, Rf 0.42, and a main ninhydrin positive component, Rf ($CHCl_3$/MeOH 9:1) 0.27. Solid potassium carbonate (280 mg, 2 mmol) was added and the mixture stirred for 1–2 hours at room temperature when t.l.c. showed a complete transformaton of the ninhydrin positive component into a faster moving product, Rf 0.48. Ammonium chloride (200 mg) was added and the mixture stirred for a few minutes before filtering and evaporation of the solvent.

The product (9) was purified on a flash column ($CHCl_3$/MeOH 95:5) to yield a solid (200 mg, 56%) which was recrystallized from ether petroleum. m.p. 110°–112° C. $[\alpha]_D^{20}$ +10.8° (c 0.83, $CHCl_3$), $\nu_{max}$ 3400 br, OH; 1670 st. amide I; 1500 amide II. Found: C, 67.17; H, 6.80; N, 3.70%. Calculated for $C_{20}H_{23}NO_5$. C, 67.21; H, 6.49; N, 3.92%.

EXAMPLE 19

5-Amino-5-deoxy-D-δ-lactam (1)

5-Amino-5-deoxy-3,6-di-O-benzyl-D-glucono-δ-lactam (9) (90 mg, 0.25 mmol) was dissolved in ethanol (5 ml). Catalytic amount of palladium black was added and the reaction stirred under hydrogen overnight. T.l.c. examination (EtOAc/MeOH/H$_2$O 4:4:1) showed a main product, Rf 0.25, some unreacted starting material, Rf 0.80, and two mono-benzyl compounds, Rf 0.68 and 0.62. More catalyst was added and the reaction left for a further 6 h when t.l.c. examination showed a complete reaction. A white solid had crystallized out. Water (3 ml) was added before the catalyst was filtered off through some celite. The solvent was evaporated to dryness. The solid residue was redissolved in minimum amount of water and the product crystallized by the addition of ethanol to yield the title product (1) 35 mg, 79%, m.p. 204°–205° C., $[\alpha]_D^{20}$ +57° (c, 0.63, water) (Lit.* 202°–204° C. des, $[\alpha]_D^{25}$ +60°, water). [*Inouye et al., *Tetrahedron* 24, 2125–2144 (1968)]. $\nu_{max}$ (KBr) broad strong signal from 3000 to 3600 with peaks at 3180, 3260, 3370, 3430, OH and NH; 1645 s.br., amide I. Found: C, 40.41; H, 6.49; N, 7.53%. Calculated for C$_6$H$_{11}$NO$_5$: C40.68; H6.26; N7.91.

Various other examples will be apparent to the person skilled in the art after reading the present disclosure without departing from the spirit and scope of the invention. It is intended that all such other examples be included within the scope of the appended claims.

What is claimed is:

1. A method for the synthesis of nojirimycin δ-lactam or deoxynojirimycin from 5,6-anhydro-3-O-benzyl-1,2-O-isopropylidene-L-idofuranose as a divergent intermediate comprising (A) forming a piperidine ring by connecting nitrogen between C-1 and C-5 of said intermediate with inversion of configuration at C-5 to form nojirimycin δ-lactam or (B) forming a piperidine ring by connecting nitrogen between C-2 and C-6 of said intermediate with inversion of configuration at C-2 to form deoxynojirimycin.

2. A method for the synthesis of nojirimycin δ-lactam comprising:
   a) Reacting 5,6-anhydro-3-O-benzyl-1,2-O-isopropylidene-L-idofuranose with sodium hydride and benzyl alcohol to give a dibenzyl idofuranose,
   b) Esterifying the free hydroxyl of the dibenzyl idofuranose with trifluoromethane sulfonic anhydride to provide a triflate,
   c) Reacting the triflate with azide ion to afford a gluco-azide,
   d) Removing the isopropylidene protecting group from the gluco-azide by acid hydrolysis, to give the corresponding lactol,
   e) Oxidizing the resulting lactol with bromine to give an azidolactone,
   f) Reducing the azidolactone by tin (II) chloride followed by treatment with potassium carbonate to provide a dibenzyl lactam, and
   g) Removing the benzyl groups in the dibenzyl lactam by palladium catalyzed hydrogenation to give nojirimycin δ-lactam.

3. A method for the synthesis of deoxynojirimycin comprising:
   a) Reacting 5,6-anhydro-3-O-benzyl-1,2-O-isopropylidene-L-idofuranose with azide ion to give an ido-azide,
   b) Reacting the ido-azide with sodium hydride, benzyl bromide and tetrabutylammonium iodide to afford a dibenzyl ether,
   c) Treating the dibenzyl ether with methanolic hydrogen chloride to give a methyl furanoside,
   d) Esterifying the methyl furanoside with trifluoromethane sulfonic anhydride to give a triflate,
   e) Reducing the triflate with tin (II) chloride to give an aminotriflate,
   f) Reacting the aminotriflate with sodium acetate to give a bicyclic amine,
   g) Reacting the bicyclic amine with benzyl chloroformate to give a protected carbamate,
   h) Subjecting the protected carbamate to acid hydrolysis, followed by reduction with sodium borohydride to give a protected deoxynojirimycin, and
   i) Subjecting the protected deoxynojirimycin to palladium catalyzed hydrogenation to provide deoxynojirimycin.

* * * * *